United States Patent [19]

Swette et al.

[11] Patent Number: 5,944,661
[45] Date of Patent: Aug. 31, 1999

[54] POTENTIAL AND DIFFUSION CONTROLLED SOLID ELECTROLYTE SENSOR FOR CONTINUOUS MEASUREMENT OF VERY LOW LEVELS OF TRANSDERMAL ALCOHOL

[75] Inventors: Larry L. Swette, Newton; Arthur E. Griffith, Lynn; Anthony B. LaConti, Lynnfield, all of Mass.

[73] Assignee: Giner, Inc., Waltham, Mass.

[21] Appl. No.: 08/840,802

[22] Filed: Apr. 16, 1997

[51] Int. Cl.$^6$ ........................................ A01B 5/04
[52] U.S. Cl. .................. 600/345; 600/346; 600/354; 600/362; 204/403
[58] Field of Search ................ 600/309, 345–348, 600/352, 354, 362, 363; 204/402, 403, 406, 407, 421

[56] References Cited

U.S. PATENT DOCUMENTS

| Re. 31,915 | 6/1985 | Oswin et al. | 204/412 |
|---|---|---|---|
| 3,824,167 | 7/1974 | Oswin et al. | 204/195 R |
| 3,824,168 | 7/1974 | Oswin et al. | 204/195 R |
| 3,838,971 | 10/1974 | Albertson | 23/232 |
| 3,909,386 | 9/1975 | Oswin et al. | 204/195 R |
| 3,966,579 | 6/1976 | Chang et al. | 204/195 R |
| 4,123,700 | 10/1978 | LaConti et al. | 324/29 |
| 4,314,564 | 2/1982 | Albarda | 128/719 |
| 4,317,453 | 3/1982 | Heim et al. | 128/719 |
| 4,499,423 | 2/1985 | Matthiessen | 324/425 |
| 4,820,386 | 4/1989 | LaConti et al. | 204/1 T |
| 4,925,544 | 5/1990 | Goldring | 204/421 |
| 4,976,135 | 12/1990 | Stock | 73/23.2 |
| 5,050,604 | 9/1991 | Reshef et al. | 600/346 |
| 5,220,919 | 6/1993 | Phillips et al. | 600/345 |
| 5,336,390 | 8/1994 | Busack et al. | 204/431 |
| 5,465,713 | 11/1995 | Schoendorfer | 600/362 |

OTHER PUBLICATIONS

Brown, D.J., *Meth. and Fin. Expltl. Clin. Pharmacol.* 1985, 7(5), 269–274.

Brown, D.J., *Meth. and Fin. Expltl. Clin. Pharmacol.* 1985, 7(10), 539–543.

Brusilow, S.W., Gordis, E.H., *Am. J. Dis. Child.*, 112, 328–333, 1966.

Jones, A.W., *J. Forensic Sci.*, 23, 283–291, 1978.

Millet, P., Machas, A., Durand, R., "A Solid Polymer Electrollyte–based Ethanol Gas Sensor," *Journal of Aplied Electrochemistry*, 26, 933–937, 1996.

Phillips, E.L.R., Little, R.E., Hillman, R.S., et al., *Alcohol Clin. Exp. Res.*, 8(2), 233–237, 1984.

Phillips, M., *Alcohol Clin. Exp. Res.*, 6(4), 532–534, 1982.

Phillips, M., *Biomater. Med. Devices Artif. Organs*, 8(1), 13–21, 1980.

Scheuplein, R.J., Blank, I.H., *Physiol. Reviews*, 51(4), 702–747, 1971.

Swift, R.M., Martin, C.S., Swette, L., LaConti, A., Kackley, N., "Studies on a Wearable, Electronic, Transdermal Alcohol Sensor," *Alcoholism: Clinical and Experimental Research*, 16(4), 721–725, 1992.

*Primary Examiner*—Jack W. Lavinder
*Assistant Examiner*—David M. Ruddy
*Attorney, Agent, or Firm*—Hale and Dorr LLP

[57] ABSTRACT

A method for continuous tracking of blood alcohol, is comprised of 1) a potential- and diffusion-controlled electrochemical solid polymer electrolyte sensor that continuously and concurrently measures very low concentrations of ethanol vapor at the surface of the skin as well as skin properties such as temperature and ionic conductivity, 2) a sensor control circuit, and 3) a data acquisition-recording device. Sensitive and reproducible measurements of ethanol over a wide population range is obtained by simultaneously maintaining the potential of the sensing electrode constant at a voltage above the rest potential of the platinum/air ($O_2$) electrode and by use of a thin, permselective diffusion-control membrane over the sensing electrode, and in series with the human stratum corneum membrane. The electrochemical oxidation current is a direct measure of the local ethanol vapor concentration over the skin surface.

13 Claims, 15 Drawing Sheets

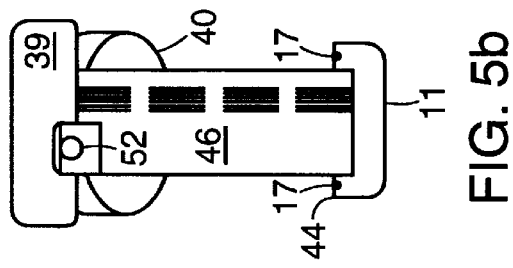
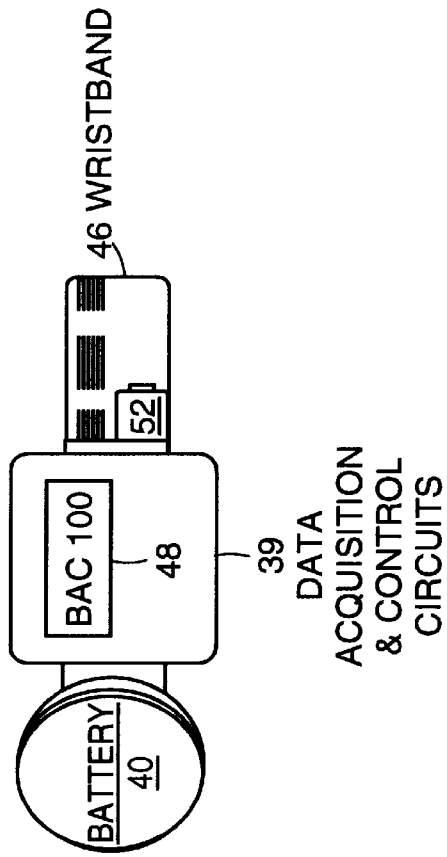
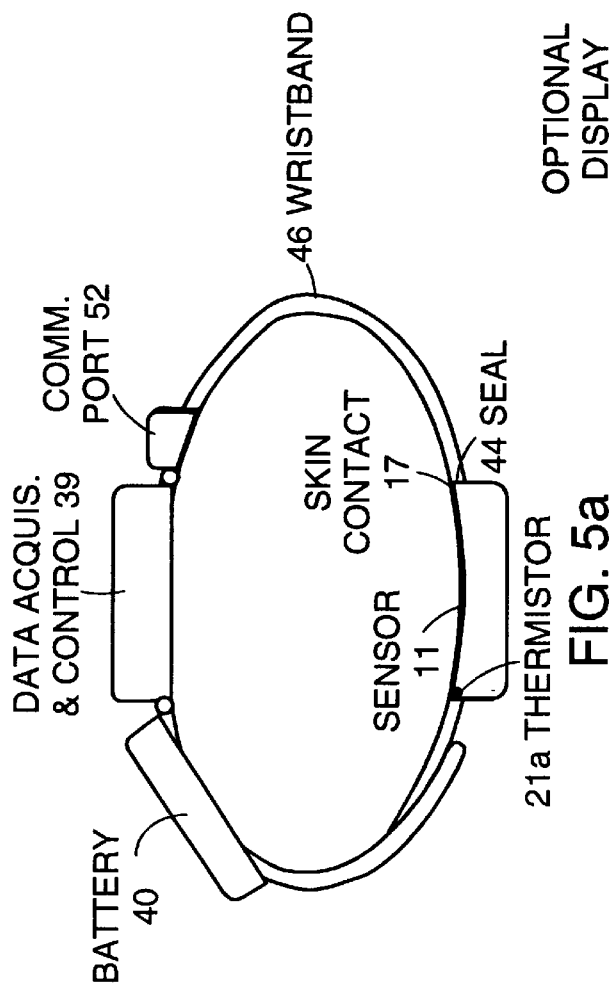

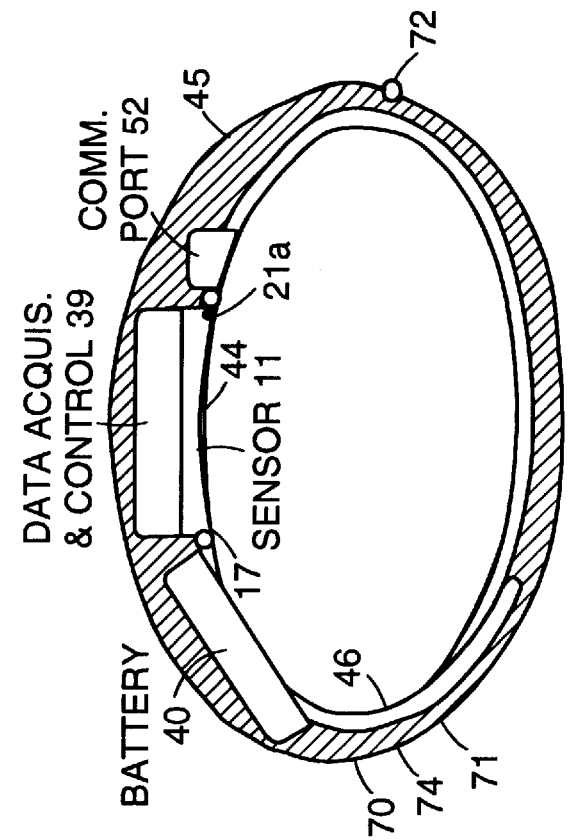
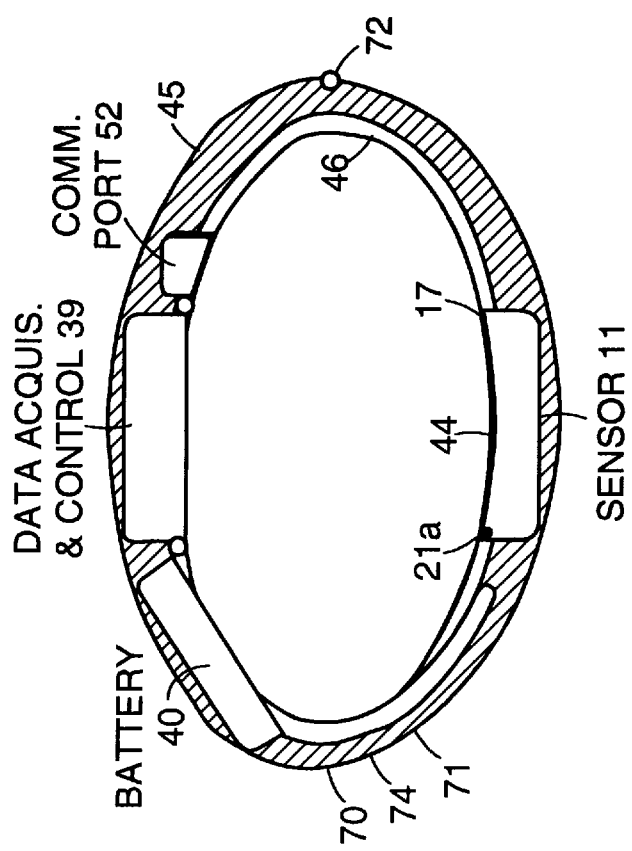
FIG. 6b
FIG. 6a

POTENTIAL AND DIFFUSION CONTROLLED SOLID ELECTROLYTE SENSOR FOR CONTINUOUS MEASUREMENT OF VERY LOW LEVELS OF TRANSDERMAL ALCOHOL

BACKGROUND OF THE INVENTION

The invention relates to transdermal alcohol sensors (TAS), and more particularly to a potential-controlled and diffusion-controlled solid electrolyte sensor for continuous measurement of very low levels of transdermal alcohol.

The reliable and valid measurement of alcohol consumption or abstinence by passive, noninvasive means, over long time periods is important for monitoring individuals in research studies, monitoring those undergoing substance abuse treatment, and for forensic monitoring in special populations. Methods traditionally used for determining alcohol consumption include verbal report measures, biochemical markers, and direct measurement of urine, blood, saliva or sweat alcohol levels. The ideal method for determining alcohol consumption would be inexpensive, highly specific and sensitive for ethanol, applicable across a wide range of users, usable over a range of time periods, and accepted by both the testers and the tested.

One promising method, the "sweat patch," of monitoring alcohol use has used the detection of ethanol transdermally. Measurable quantities of ingested ethanol are excreted through the human skin, by exocrine sweat glands, and by diffusion across the skin. Transdermal ethanol levels generally reflect blood levels.

The alcohol dosimeter or "sweat patch" is a wearable, noninvasive device which is reported to accumulate ethanol in an absorbent medium to assess cumulative ethanol consumption over a 7- to 10-day period. However, field trials of the sweat patch identified problems limiting its clinical utility. These include problems with ethanol storage and losses due to evaporation, back-diffusion and bacterial metabolism.

Electrochemical detection of ethanol has been used for many years in sensor cells which oxidize ethanol and produce currents proportional to the ethanol concentration. Such cells are used in commercially available portable breathalysers (e.g., Alco-Sensor III by Intoximeters, Inc., St. Louis, Mo.). The readings are well correlated with blood alcohol concentration (BAC). Application of this device to periodically measure alcohol accumulated in sweat-patch experiments, as described above, does not supply continuous alcohol consumption data.

Methods and apparatus for determining alcohol concentration in blood using electrochemical breath alcohol measurements are extensive and examples of these are described in U.S. Pat. Nos. 3,824,167; 3,824,168; 3,838,971; 3,909,386; 3,966,579; 4,314,564; 4,317,453; 4,499,423; Re. 31,915; 4,925,544; 4,976,135; 5,336,390. Most of these processes use liquid electrolytes or solid gelled liquid electrolytes containing an ionic salt or acid. A solid polymer electrolyte electrochemical cell, containing no liquid electrolyte, has also been used for the detection of alcohol as described in U.S. Pat. No. 4,820,386.

The typical breath alcohol sensing devices, such as the devices sold by Intoximeter (St. Louis, Mo.), measure alcohol concentrations present in a gaseous breath sample by measuring the magnitude of the short circuit current passing through the external circuit between the anode and cathode of a fuel cell. The potential of the anode (or sensing electrode) prior to ethanol exposure is determined by the air ($O_2$) cathode and will change depending on the oxidation current due to alcohol consumption on the anode. The sensing anode potential is not fixed or controlled. It drifts below the Pt/air ($O_2$), 1.06 V rest potential (vs. a Normal Hydrogen Electrode, N.H.E.) when current passes from the sensing anode to the air cathode. A potentiostatic method of controlling the sensing electrode at a fixed potential above the potential of a Pt/air ($O_2$) reference electrode located on the same piece of solid polymer electrolyte membrane is described in U.S. Pat. No. 4,123,700. Several of the breath alcohol sensors described above utilize 1) methods for mechanically introducing, periodically, a fixed amount of breath alcohol into sample chambers or 2) detection methods to indicate breath alcohol is validly being sampled (e.g., water vapor detectors, pressure switch). The detection and sampling processes are not applicable to the accurate and reproducible continuous monitoring/recording of transdermal alcohol vapor.

No single method currently exists to easily and reliably quantify patterns of alcohol consumption or abstinence over a period of days, weeks or months. Existing commercial electrochemical sensors are not suitable for continuous and reliable longterm measurement of alcohol. They are not sufficiently sensitive, selective, reproducible, or passive (i.e., they require active subject participation).

Therefore it is a principal objective of this invention to provide an electrochemical sensor based on a solid polymer electrolyte in the proton exchange form integrated with a recording device that is wearable and provides 1) continuous rather than episodic monitoring of blood alcohol levels by passive tracking of very low concentrations of transdermal alcohol, and 2) selective, accurate, semiquantitative and temporal tracking of ethanol consumption or abstinence over extended periods.

Still another object of this invention is to provide a process and method for continuously monitoring transdermal ethanol by an electrochemical solid polymer electrolyte sensor, which includes the sensor cell, diffusion-control membrane and potential-control circuitry and a data acquisition-recording device unitized into a single instrument.

Still another object of this invention is to provide a solid polymer electrolyte sensor and process that provides potential and diffusion control to the sensor cell, leading to rapid electrochemical oxidation of ethanol and establishment of a steadystate flux of ethanol from skin to sensing electrode surface.

Still another object of this invention is to have an integral diffusion-control membrane over the sensing electrode that is in series with the human stratum corneum and 1) controls ethanol and water flux from the skin contact area to the solid polymer electrolyte sensor cell and normalizes ethanol permeation differences due to the skin properties and 2) helps manage humidification of the sensor cell solid polymer electrolyte membrane.

Still another object of this invention is to provide a solid polymer electrolyte sensor that concurrently, with transdermal alcohol measurement, also measures skin properties such as temperature and ionic conductivity to determine continuous contact with the skin.

SUMMARY OF THE INVENTION

A transdermal alcohol sensing instrument for the continuous tracking of blood alcohol, is comprised of 1) a potential- and diffusion-controlled electrochemical solid polymer electrolyte membrane sensor assembly that has all the sensor cell electrodes in intimate contact (e.g., bonded) with the proton exchange membrane and continuously and concurrently measures very low concentrations of ethanol vapor at the surface of the skin as well as skin properties such as temperature and ionic conductivity, 2) a sensor control circuit that maintains the sensing electrode potential constant versus a stable reference or counter electrode, with all the electrodes located on the same film of solid polymer electrolyte membrane, and 3) a data acquisition-recording device. Sensitive and reproducible measurements of ethanol over a wide population range is obtained by simultaneously maintaining the potential of the sensing electrode constant at a voltage above the rest potential of the platinum/air ($O_2$) electrode and by use of a thin, permselective diffusion-control membrane over the sensing electrode, and in series with the human stratum corneum membrane. The electrochemical oxidation current is a direct measure of the local ethanol vapor concentration over the skin surface.

These and other objects and features in the present invention will be more fully understood by the following detailed description, which should be read in light of the accompanying drawings in which corresponding reference numerals refer to corresponding parts through the several views.

BRIEF DESCRIPTION OF THE DRAWINGS

FIGS. 5(a), 5(b), and 5(c) are a plan, side, and top view, schematic representation of a miniaturized embodiment of the transdermal alcohol sensor shown in FIG. 1 for wearing on a wrist, arm or leg;

FIGS. 6a and 6b are schematics of alternative embodiments of a miniaturized transdermal alcohol sensors for wearing on the wrist, arm or leg;

DETAILED DESCRIPTION OF THE PREFERRED EMBODIMENTS

Figure 1:
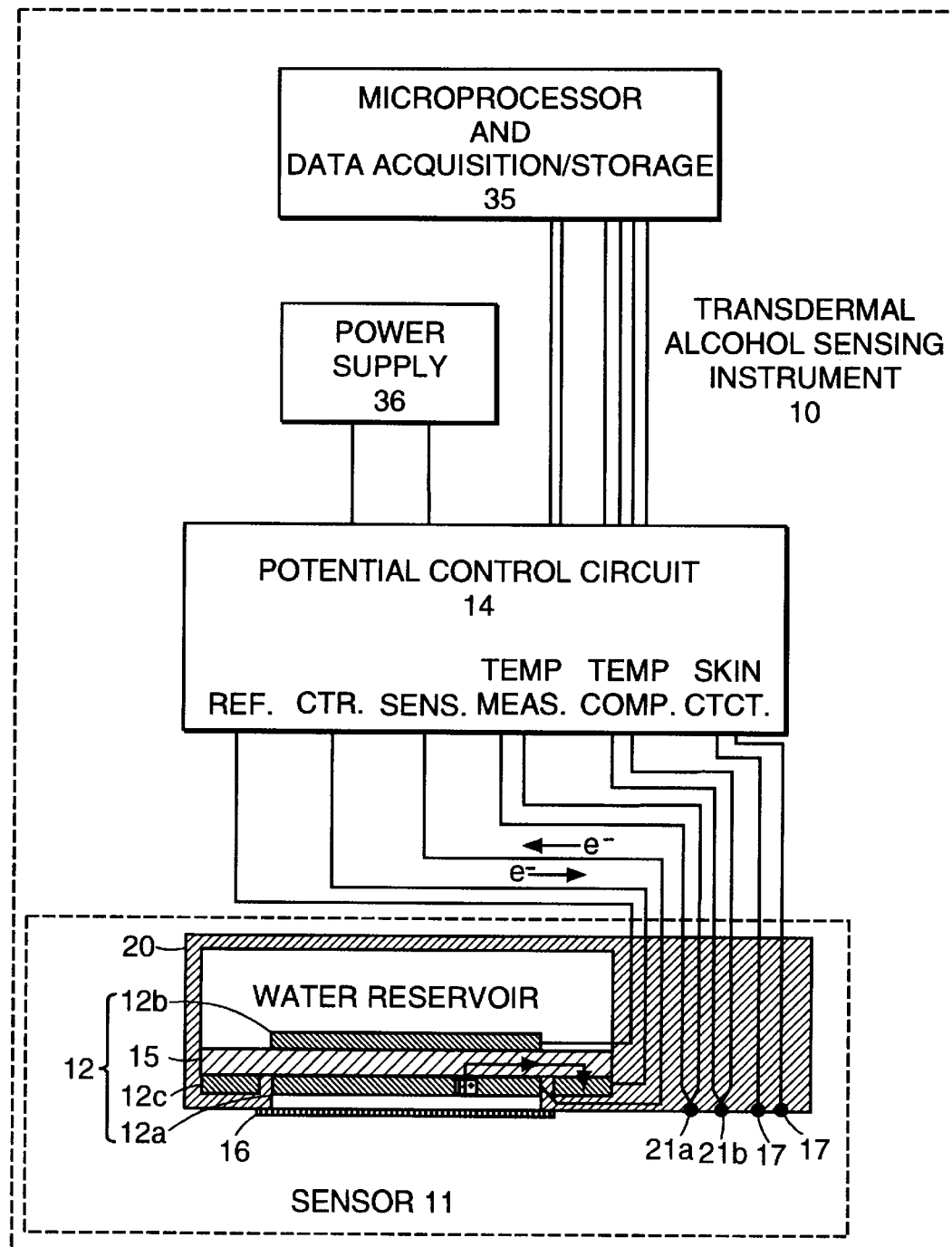
FIG. 1 is a schematic block diagram of the component parts of the transdermal alcohol sensing instrument of the present invention.

Referring to FIG. 1, the transdermal alcohol sensing instrument 10 of the present invention for continuously measuring transdermal ethanol utilizes an electrochemical solid polymer electrolyte sensor assembly 11 that detects ethanol vapor. The TAS instrument 10 includes a sensor assembly 11 consisting of three-electrode, potential-controlled sensor cells 12, and a diffusion-control membrane 16 enclosed in a housing 20, potential-control circuitry 14, and a data acquisition-recording device 35, unitized into a single sensing instrument 10.

The sensing electrode 12a, counter electrode 12c, and reference electrode 12b are all TEFLON bonded electrodes (TBE) comprised of commercially available fuel cell grade platinum black, S3002 (Engelhard Corp., Seneca, S.C.) bound together with particles of polytetrafluoroethylene (PTFE) from TEFLON product Type 30 dispersion (E.I. Du Pont, Washington, W.Va.). Typically the electrodes are thermally processed in an oven at 300 to 350° C. for 15 to 60 minutes to sinter the PTFE and remove residual wetting agents from the type 30 dispersion. Alternatively, solid polymer ionomer particles from a NAFION® 1100 (1100 equivalent weight) solution (Solutions Technology, Mendenhall, N.J.) could be used as a binder for the platinum black in place of, or together with the TEFLON particles. The NAFION particles have an advantage since they are proton conductors and readily absorb water, helping to maintain the sensor cell membrane and electrode assembly properly humidified. All three electrodes are integrally bonded to the same film of solid polymer electrolyte membrane 15 in the proton exchange form. Typical pressing times and conditions are 15 to 30 minutes using temperatures of 250 to 350° C. and pressure of 600 to 1200 psi.

As shown in FIG. 1, the sensor cell 12 contains a permselective diffusion-control membrane 16 of low-density polyethylene sold by Goodfellow Corp. (e.g., #ET 311115), Berwin, Pa., over the sensing electrode 12a. When being used, the open face of the sensor 11 assembly segment of the instrument 10 is placed over the skin surface and continuously oxidizes ethanol in the manner described below. When mounted adjacent to human skin, the integrated potential-controlled sensing electrode 12a and diffusion-control membrane 16 is in series with the human stratum corneum membrane and controls the ethanol flux to the sensing electrode surface.

Referring to FIG. 1, at the sensing electrode 12a, the ethanol vapor in equilibrium with the skin is instantaneously electrochemically oxidized to acetic acid with concomitant release of electrons to the current sensing branch of the potential-controlling circuit 14 or "potentiostat," and the formation of protons that are electrochemically transported through the solid polymer electrolyte film 15 (proton exchange membrane) to the counter electrode 12c. At the counter electrode 12c, the protons combine with oxygen from the air and the external electrons which are electrons released from the sensing electrode 12a and pass through a current sensing branch (a resistor) of the potentiostat and return to the counter electrode 12c to form water at the counter electrode 12c. The corresponding electrochemical reactions are as follows:

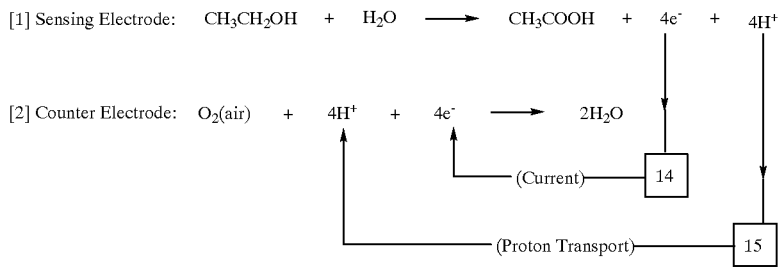

Figure 8:
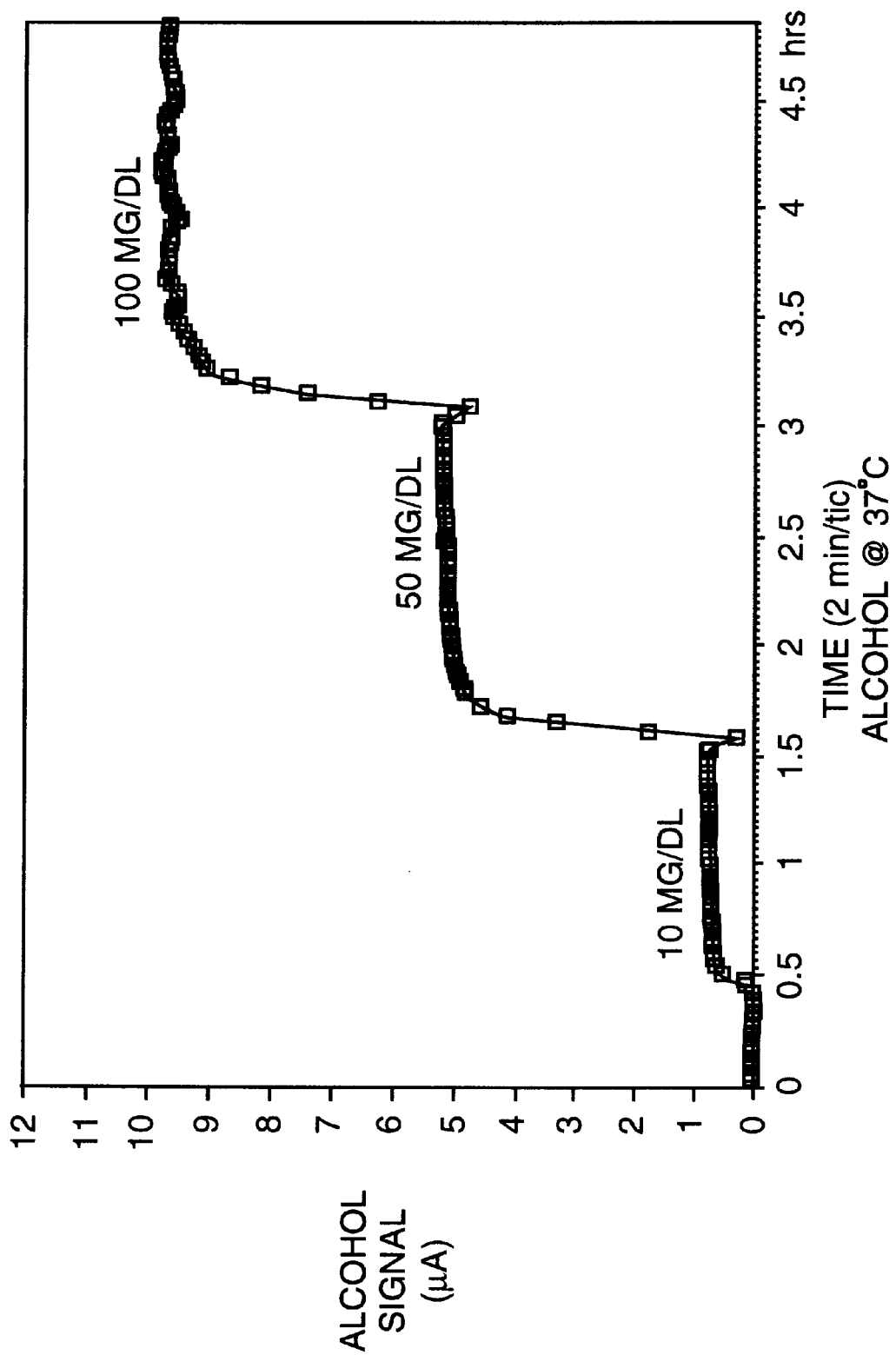
FIG. 8 is a graph of the ethanol vapor response of the in vitro alcohol sensor shown in FIG. 1 with a diffusion-controlled membrane.

The electrochemical ethanol oxidation current is used as a direct measure of the local ethanol vapor concentration. This current is measured as electrons are released from the sensing electrode 12a to the external potentiostat circuit and then pass through a resistor producing a voltage signal proportional to ethanol vapor concentrations. The correlation between current and ethanol vapor concentration is shown in FIG. 8. The sensor is highly responsive to ethanol and unresponsive to potential interferants such as oxygen, carbon dioxide and acetone. The sensing electrode 12a is maintained through potentiostatic-control near the Pt/air ($O_2$) rest potential (1.06 V a N.H.E). At this potential, oxygen from the air does not electrochemically react. Also, $CO_2$ is completely inert and acetone is highly unreactive and gives a negligible signal at this potential and skin temperature.

Two thermistors (Beta Therm (100K6A1) Shrewsbury, Mass.) 21a, 21b, embedded in the plastic housing 20 near the skin surface produce temperature signals, which are used to determine that the device is in continuous contact with the skin and to compensate for changes in ethanol diffusion rate through the diffusion-control membrane 16 with temperature changes. The sensor also uses integral galvanic microelectrodes 17 consisting of two platinum pins 17a, 17b mounted in the sensor housing at the sensor cell/skin interface to measure skin ionic conductivity, and therefore indicate any loss of contact with the skin. The galvanic microelectrodes 17 are fabricated from 0.5-mm-diameter Pt-10% Ir wire. The pins are mounted 0.100 inches apart with about half of the surface of the 1 mm diameter spherical tips exposed. This Pt-10% Ir wire is commercially available from Engelhard Industries, with the skin-interface tip melted into a spherical shape about 1 mm in diameter to provide a smooth non-irritating surface.

Figure 2:
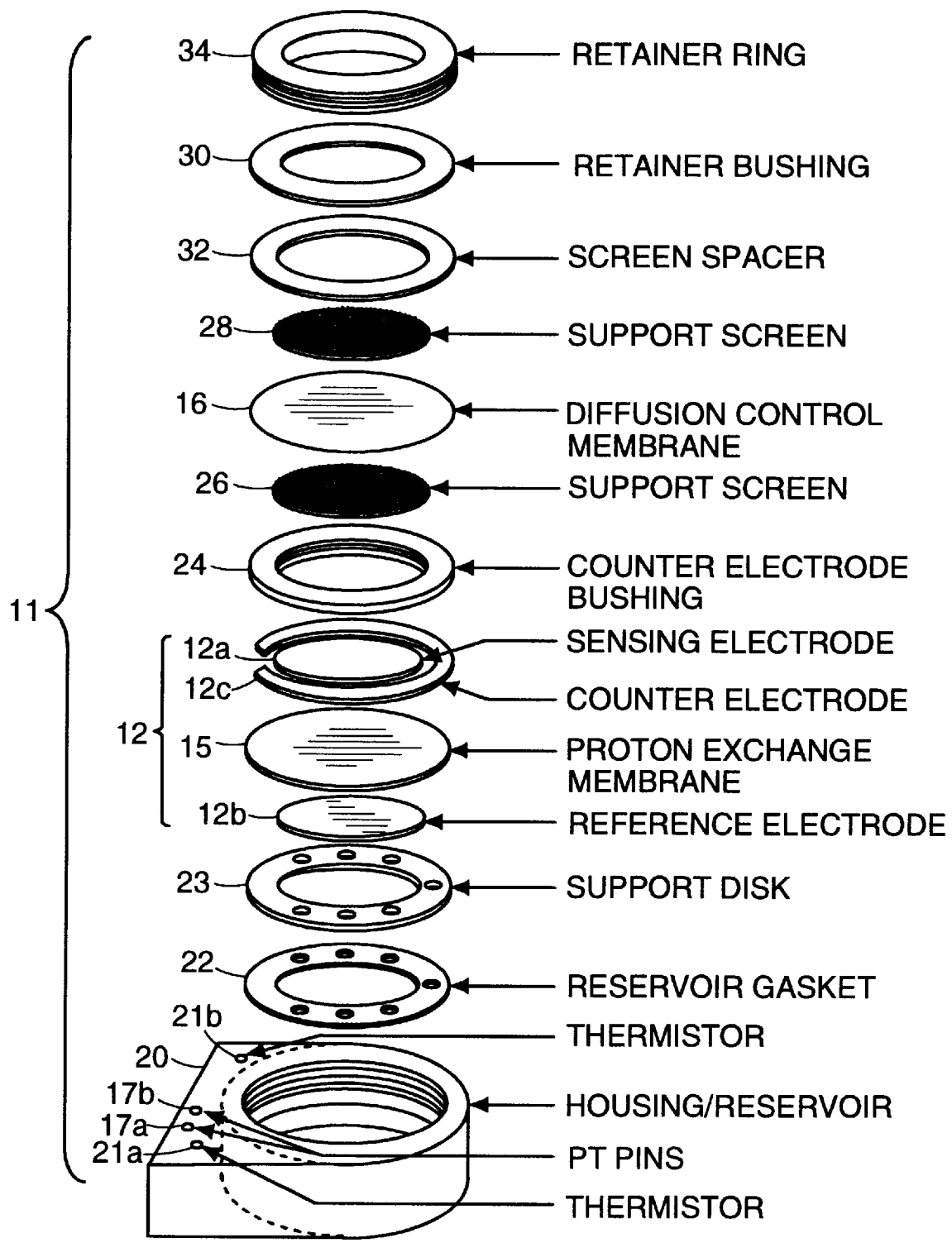
FIG. 2 an exploded perspective view of a preferred embodiment of the alcohol sensor assembly shown in FIG. 1.

The preferred embodiment of a transdermal alcohol sensor assembly 11 of the present invention is shown in FIG. 2. Sensor assembly 11 includes a housing 20 in which a reservoir gasket 22 seals the water reservoir. A thin annular disk with holes 23 provides support for the sensor cell 12. As mentioned above, the sensor cell 12 includes three electrodes: a sensing electrode 12a, a reference electrode 12b and a counter electrode 12c. The arrangement of these three electrodes is shown in FIGS. 1 and 2. In a preferred embodiment of this invention, the sensing electrode 12a and counter electrode 12c are bonded to the same side of the membrane 15 as shown in FIG. 2, or alternatively, all three electrodes 12a, 12b and 12c can be bonded to the same side of the membrane 15. A counter electrode bushing 24 is mounted over sensor cell 12 and provides a platform for the lower support screen 26. The diffusion-control membrane 16 is positioned over the lower support screen 26 and another support screen 28 rests on top of the diffusion control membrane 16 within a screen spacer 32. A retainer bushing 30 is placed over the screen spacer 32 and a threaded retainer ring 34 holds the components together inside the matching threaded housing 20.

The transdermal alcohol sensing instrument 10 which includes the sensor assembly 11, a diffusion-control membrane 16 potential-control circuitry 14 and the data acquisition-recording device 35, are unitized into a single alcohol sensing instrument 10. The instrument 10 is preferably battery operated, and has the ability to sample the ethanol, temperature signals, and skin contact measurements at intervals and store in the random access memory (RAM) 35b on the data acquisition board 35 days to weeks of data. The data acquisition circuit microprocessor 35a is programmed to sample and store the three signals (ethanol concentration, temperature and skin contact), at preset intervals. Data are off-loaded to a personal computer by accessing the data acquisition microprocessor/RAM storage 35b through an RS232 port 35c.

Figure 3:
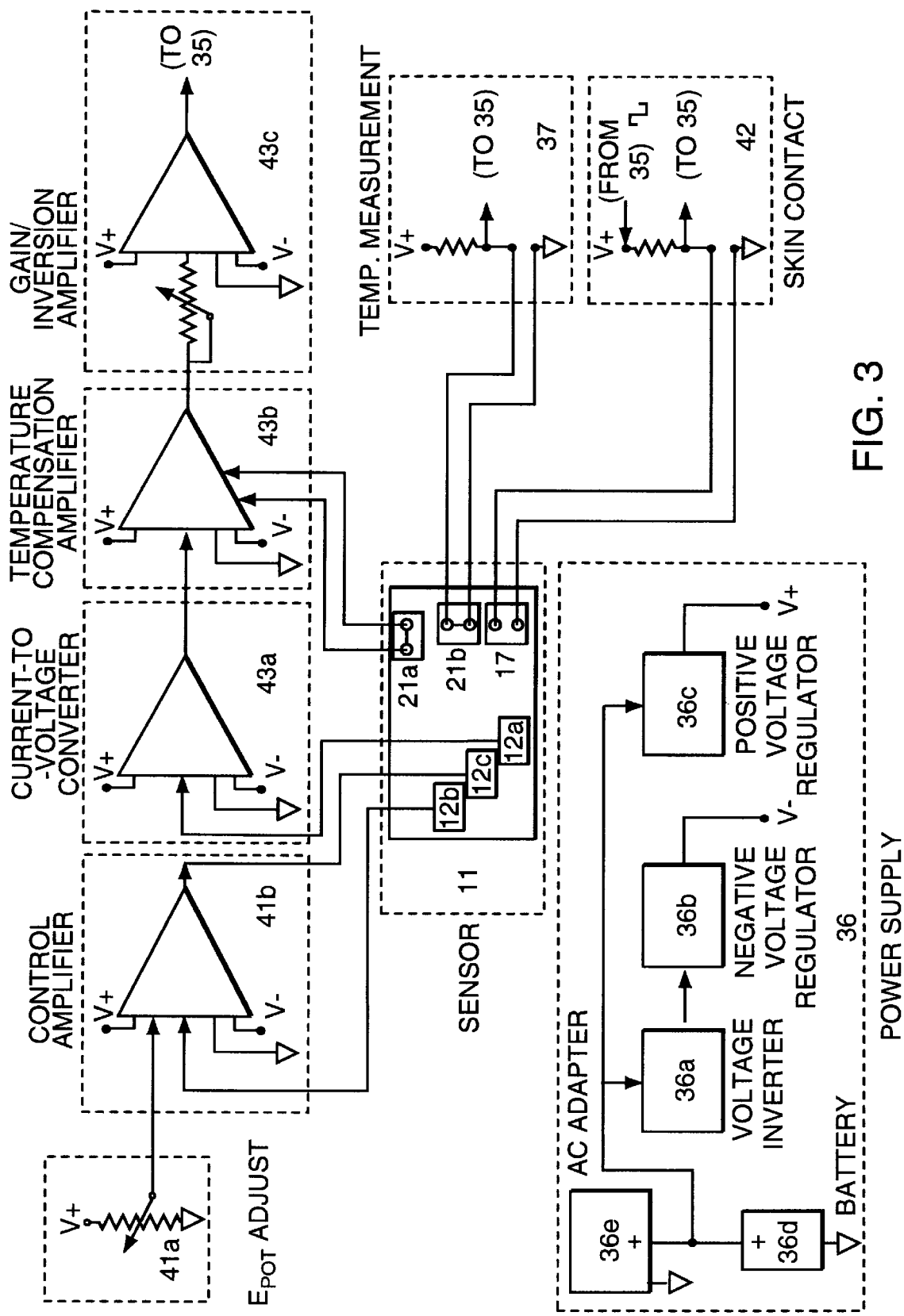
FIG. 3 is a schematic of the ethanol sensor control circuit for management of analog control signals and analog data used in the sensing instrument shown in FIG. 1.

The novelty of the measurement process is that it features potential (voltage) control as well as diffusion control of the sensor cell for the sensitive and reproducible measurement of alcohol vapor permeating through the skin. Also, the unique solid polymer electrolyte sensor cell uses the water vapor from the skin to maintain hydration of the solid polymer electrolyte membrane for proton transport; there is no liquid electrolyte present. Water vapor permeates from the body through the skin and helps maintain the polymer sulfonic acid groups hydrated so they can effectively transport protons. The potential-control circuit 14 (potentiostat) maintains the sensing electrode 12a at a fixed potential above the reference electrode 12b by passing current between the sensing 12a and counter electrode 12c. All three electrodes are located, on the same film of solid polymer electrolyte. A typical potentiostatic circuit for maintaining the sensing electrode 12a at a fixed potential versus a Pt/air ($O_2$) reference 12b is shown in FIG. 3. The preferred potential range for the sensing electrode 12a is 0 to 50 mV above the Pt/air ($O_2$) reference (1.06 to 1.11 V above a N.H.E.). The useful potential-control range to avoid or minimize interference from air ($O_2$), is 0 to 300 mV above the Pt/air ($O_2$) reference. In this potential range, the sensing electrode 12a has a thin oxide layer on its surface and ethanol is electrochemically oxidized very rapidly and completely; there is essentially zero concentration of ethanol at the sensing electrode 12a surface. The combined process of potential and diffusion control of the sensor cell 12 creates a concentration gradient from the skin to the sensing electrode 12a surface and results in a steady-state flux of alcohol and rapid electrochemical oxidation, related to blood alcohol concentration (BAC).

Referring to FIG. 3, a block diagram of the ethanol sensor control circuit 14 is shown. The ethanol sensor control circuit 14 is designed to: (1) control the potential of the ethanol sensor electrode 12a at a predetermined voltage (the "potentiostatic voltage", or "$E_{pot}$"); (2) convert the ethanol concentration-related current to a temperature compensated voltage signal; (3) measure the skin temperature; (4) measure the skin resistance; and (5) provide properly amplified voltage to the data acquisition/storage board 35. An on-board micro power regulated power supply 36 uses the data acquisition/storage board's 35 power supply 36 to provide the required ±3.9 volts for the sensor circuitry. The DC power can be supplied by a 6 V battery 36d or an AC adaptor 36e.

or 28L) through a micro power regulated power supply 36. The power supply 36 utilizes a voltage inverter (e.g., ICL 7660) 36a to convert the positive battery voltage to a negative voltage of the same magnitude, and a positive voltage regulator (e.g., MAX 663) 36c and negative voltage regulator (e.g., MAX664) 36b to provide a stable ±3.9 volts.

The total analog circuitry draws less than 100 µA from the battery. 36d

The electrochemical reactions are as follows:

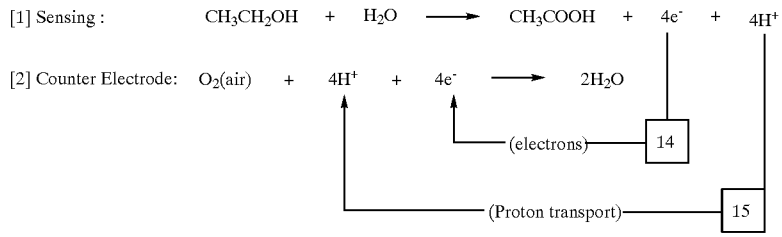

The control amplifier portion 41b of the potentiostat circuit 14 consists of a micro power operational amplifier (e.g., MAX407 or LM6062). The sensing 12a, counter 12c and reference 12b electrode portions of the "cell" 12 are in the feedback loop of the control amplifier 41b as shown in FIG. 3, a standard configuration for potentiostat circuits. An adjustable voltage divider 41a allows the polarizing voltage ($E_{pot}$) to be set within a 0- to 50-mV range. This signal is compared to the reference electrode 12b voltage (which appears with it at the summing junction) by the control amplifier 41b of the potentiostat circuit 14. The latter adjusts the current through the cell 12 to minimize the difference between the $E_{pot}$ and the reference electrode 12b voltages.

The resulting sensor cell 12 current (flow of electrons from 12a to 12c), which is linearly related to the concentration of ethanol, is transformed to a voltage signal by the current-to-voltage converter 43a. Temperature compensation of the sensor signal is effected in the next stage of amplification 43b, using a thermistor 21a which is positioned in the ethanol sensor plastic housing 20 near the skin surface. The last stage of amplification 43c provides the necessary inversion of the voltage signal as well as gain adjustment, to permit calibration for normal variations in sensitivity among sensors. The same type of micro power operational amplifier is used for these stages 43a, 43b, 43c as for the control amplifier 41b. The transformed current signal is directed to A/D channel 0 on the data acquisition board 35 shown in FIG. 4.

Skin temperature is monitored by a second thermistor 21b which is also incorporated into the face of the sensor. The thermistor 21b is part of a voltage divider 37 connected between $V^+$ and ground; the voltage across the thermistor 21b is directed to AID channel 1 on the data acquisition board 35. A circuit 42 similar to that for temperature monitoring is used for detecting and measuring the skin resistance. In this case, however, a pair of exposed platinum pin sensors 17 located on the front surface of the sensor assembly 11 is used. Also, the skin contact divider circuit 42 is activated by an AC signal provided by the data acquisition board 35. The resulting AC voltage across the platinum pin electrodes 17a and 17b is directed to A/D channel 2 on the data acquisition board 35.

Figure 4A:
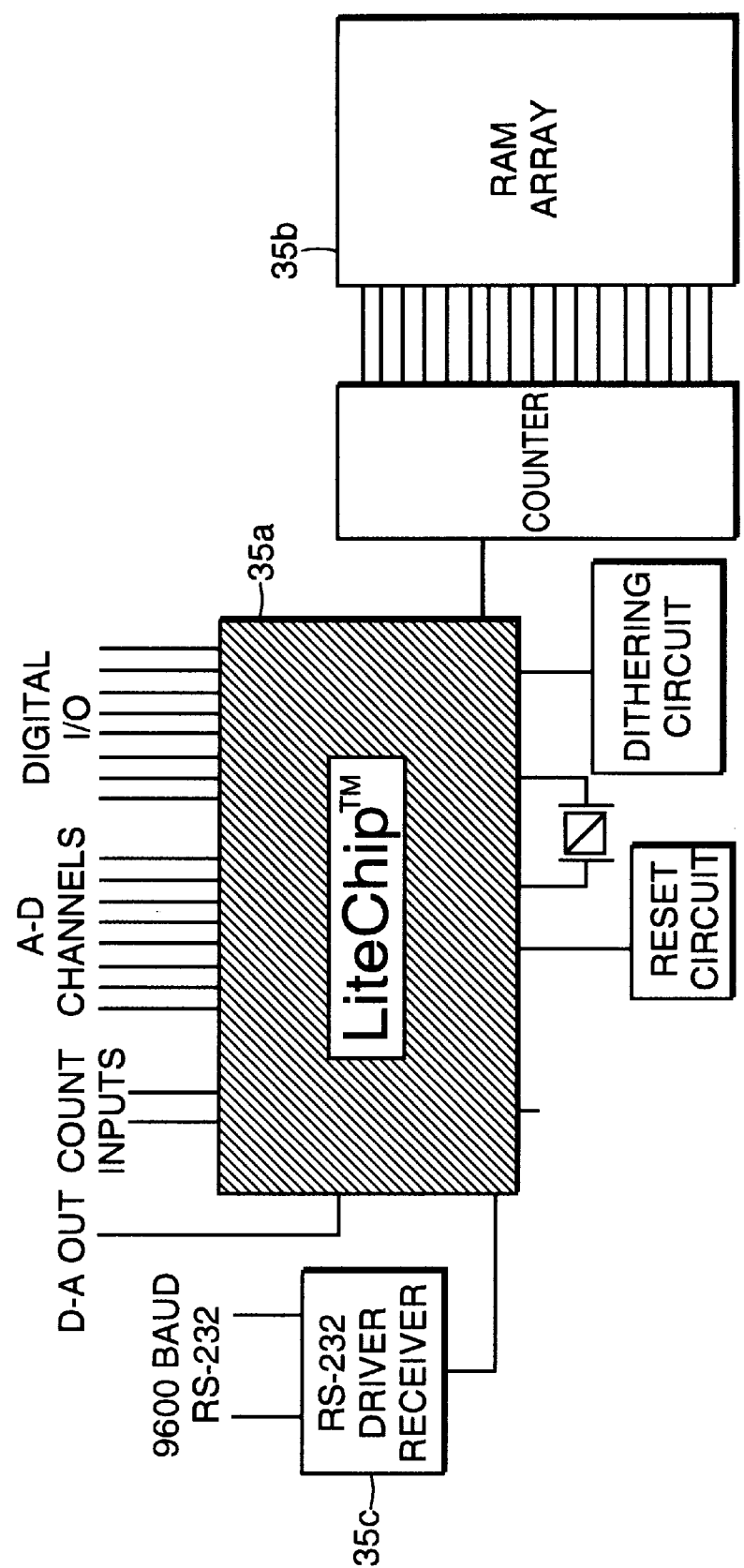
FIGS. 4(a) and 4(b) are schematic diagram of the data acquisition storage circuit used in the sensing instrument shown in FIG. 1.
Figure 4B:
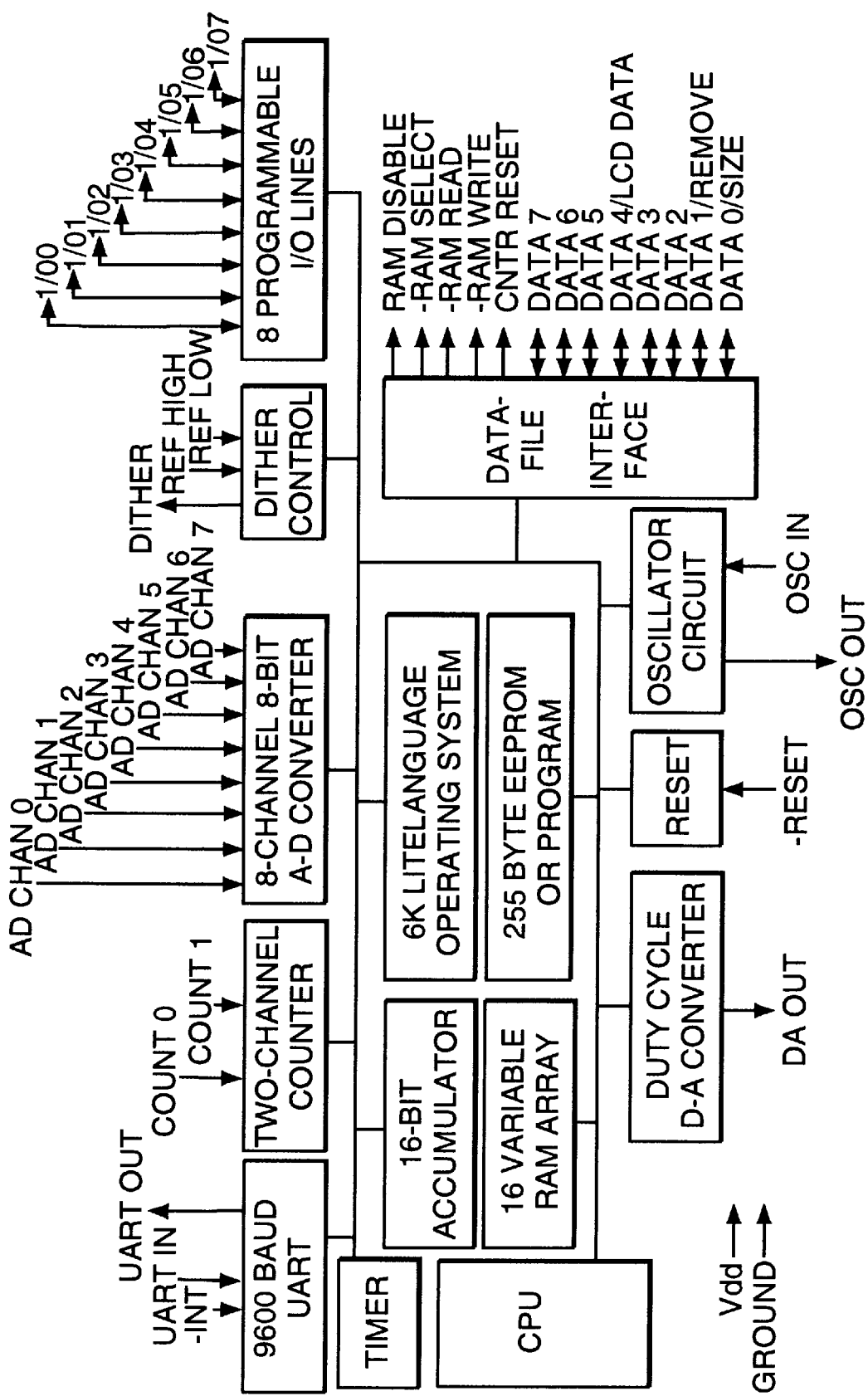

Power for the potentiostat 14 and other analog circuitry (37, 42) is provided by a Duracell 6-V battery 36d, (PX 28A Protons are transported internally from the sensing electrode 12a to the counter electrode 12c via proton-conducting solid polymer electrolyte membrane 15 as shown in FIG. 1. Water vapor permeates from the body through the skin and helps maintain the polymer membrane sulfonic acid groups hydrated so they can effectively transport protons. A typical solid polymer electrolyte membrane 15 that has been successfully used is NAFION® 117 sold by DUPONT (Wilmington, Del.). Current passing from the sensing electrode 12a to the counter electrode 12c flows through an external control circuit 14 as shown in FIG. 3, where it is converted to a voltage output signal which is amplified and stored in an integral data acquisition-recording device 35, as shown in FIG. 4, or a remote recording and storage station or unit.

The sensing electrode 12a is covered with a thin diffusion-control membrane 16 that has a lower permeability to ethanol than the skin. The membrane 16 is selected such that it is sufficiently diffusion limiting relative to skin so that it normalizes ethanol permeation differences due to the skin properties and makes it applicable over a wide range of users. Another function of the permselective membrane 16 is to control water-vapor flux from the skin to the solid-electrolyte-membrane sensor cell 12 and help manage humidification of the proton exchange membrane 15. A typical configuration for the diffusion-control membrane 16 is a polyethylene film having a thickness of 1 to 50 micrometers. The preferred thickness for the diffusion-control membrane 16 is 2 to 15 micrometers. A typical example is a low-density polyethylene film sold by Goodfellow Corp. (e.g., #ET 311115), Berwin, Pa.

With the potential- and diffusion-controlled sensor cell 12, the ethanol is rapidly oxidized to acetic acid and the effective ethanol concentration of the surface of the sensing electrode 12a is zero. The establishment of a steady-state flux and also the normalizing effect of the diffusion-control polyethylene membrane 16 of approximately 7.6 micrometer thickness is shown below when detecting 100 mg/deciliter (dl) ethanol at 37° C.

The calculated sensor cell 12 response signal with (a) and without (b) the diffusion-control membrane 16 is as follows:

a) Without a diffusion-control membrane 16 with diffusion across an air gap, d:

$$C_{air} = 10^{-8} \text{ moles/cm}^3; D_{air} = 0.1 \text{ cm}^2/s$$

$$I_{air} = \frac{n \cdot F \cdot A \cdot D_{air} \cdot C_{air}}{d}$$

where: n=equivalents/mole of ethanol=4
F=Faraday's Constant (96,500 coulombs/equivalent)

$$= 1100 \text{ } \mu A \quad \text{when} \quad A = 3.88 \text{ cm}^2$$
$$\text{and} \quad d = 1.3 \text{ cm}$$
$$= 11 \text{ } \mu A \text{ per mg/dl}$$

b) With a 7.6-micrometer-thick diffusion-control membrane 16 (Mbn):

$J_{Mbn}=5.45\times10^{-12}$ moles/cm$^2$-sec
at 100 mg/dl and 37° C.

Corresponding current signal for a sensing electrode 12a of area, A:

$$I_{Mbn} = n \cdot F \cdot A \cdot J_{Mbn}$$
$$= 8 \text{ } \mu A \text{ when } A = 3.88 \text{ cm}^2$$
$$= 0.08 \text{ } \mu A \text{ per mg/dl}$$

These values are consistent with experimental data

The comparative calculated sensor cell signal through the stratum corneum (c) when detecting the same 100 mg/dl, 37° C. is shown below.

c) Ethanol diffusion through human stratum corneum (outer skin layer):

$$J_{SKIN} = 1.15 \times 10^{-11} \text{ moles/cm}^2\text{-sec}$$
$$\text{at } 100 \text{ mg/dl and } 37° \text{ C.}$$

(extrapolated value; from Sheuplein, R.J., Physiol. Reviews, 51(4), 702–747, 1971)

Corresponding current signal for a sensing electrode 12a of area, A:

$$J_{SKIN} = n \cdot F \cdot A \cdot J_{SKIN}$$
$$= 17 \text{ } \mu A \quad \text{when } A = 3.88 \text{ cm}^2$$
$$= 0.17 \text{ } \mu A \text{ per mg/dl}$$

The effective flux (d) through the skin and diffusion-control membrane is shown below.

Effective flux of ethanol through skin and diffusion-control membrane 16:

$$\frac{1}{J_{EFF}} = \frac{1}{J_{SKIN}} + \frac{1}{J_{Mbn}}$$

Corresponding current signal with a 7.6-micrometer-thick membrane 16:

$$I_{EFF} = n \cdot F \cdot A \cdot J_{EFF}$$
$$= 5.5 \text{ } \mu A \quad \text{when } A = 3.88 \text{ cm}^2$$
$$= 0.055 \text{ } \mu A \text{ per mg/dl}$$

The corresponding membrane attenuation factor:

$$\frac{I_{SKIN}}{I_{EFF}} = \frac{0.17 \text{ } \mu A \text{ per mg/dl}}{0.055 \text{ } \mu A \text{ per mg/dl}} = 3$$

For calibration, a 4:1 ratio is used in the preferred embodiment. For example, the transdermal alcohol sensing instrument 10 is set to read 400 mg/dl when measuring 100-mg/dl ethanol solution in vitro.

Human-subject measurements were conducted with the transdermal alcohol sensing instrument 10 to confirm the order of magnitude calculated projection based on ethanol diffusion through the skin. The in vitro measurements were conducted with no membrane 16 over the sensing electrode 12a and the measurements with subjects were conducted with a 7.6-micrometer ($\mu$m) membrane 16.

Data for 6 Subjects and 3 Different Sensors 11

|  | No Membrane | 7.6-$\mu$m Membrane 16 |
| --- | --- | --- |
| Average signal ($\mu$A per mg/dl) | 0.170 | 0.046 |
| Calculated signal ($\mu$A per mg/dl) | 0.170 | 0.055 |

Experimental results suggest an in-vitro-to-transdermal ratio of approximately 4:1.

The transdermal alcohol sensing instrument 10 includes three unitized battery-powered components: (1) an electrochemical sensor assembly 11 which includes a sensor cell 12 that detects ethanol vapor at the surface of the skin, temperature monitor 37 and skin contact monitor 42, and (2) a sensor potential-control circuit 14, and (3) a data acquisition-recording device 35. The sensor cell 12, which is potential-controlled and has a diffusion-limiting membrane 16, is placed over the skin surface and continuously oxidizes excreted ethanol, in the presence of water, while the water is regenerated at the counter electrode 12c by reduction of dissolved oxygen (from ambient air).

The resultant oxidation current is a direct measure of the ethanol impinging on the sensing electrode 12a. The ethanol flux to the sensing electrode 12a is attenuated by the two membranes in series, first the stratum corneum layer of the human skin, and second the diffusion limiting membrane 16 in front of the sensing electrode 12a, which is used to reduce the effect of individual skin variations. This results in a response time shift relative to blood alcohol values over and above the time for ethanol to diffuse from the blood through tissue to the skin interface. In addition, two thermistors 21a, 21b Beta Therm (#100K6A1), Shrewsbury, Mass., are imbedded in the plastic housing 20 near the skin surface to monitor the continuous contact between skin and the device, and to compensate for changes in ethanol diffusion rate through the membrane 16 with temperature changes. The sensor also uses galvanic microelectrodes 17 consisting of two platinum pins 17a, 17b mounted in the sensor housing 20 at the sensor cell/skin interface to indicate ionic conductivity and therefore indicate any loss of contact with the skin.

Studies on potential interferants found in the body, such as oxygen, carbon dioxide, or acetone revealed no effect on the sensor alcohol signal.

A block diagram of the complete alcohol sensing instrument 10 is shown in FIG. 1. A schematic of the ethanol sensor control circuit is shown in FIG. 3. The sensor assembly 11 and its potentiostat-control circuit 14 are integrated with a battery-operated data acquisition-recording device 35 shown in FIG. 4, (32K memory), which samples ethanol, temperature, and skin contact signals at 10-, 20-, or 30-second intervals and stores an average value at intervals of 2, 5, or 10 minutes according to a programmable protocol. The data acquisition/storage device 35 can record 8 days of data, storing at 2-minute intervals, or up to 40 days storing at 10-minute intervals. In clinical testing to date, a 2-minute interval is suitable for one-day clinical studies and a 10-minute interval is appropriate for extended wear. The data acquisition/logic circuit 35 is programmed to sample three analog signals from the control circuit 14, convert these to digital signals and store the three signals (ethanol concentration, temperature and skin contact) at preset intervals together with real time data. Data are off-loaded to a personal computer by accessing the data acquisition microprocessor/RAM storage 35b through a RS232 port 35c. After downloading, the digital data are converted to engineering units of temperature and BAC, and graphed by a menu-driven LOTUS® 123 spreadsheet. Through a potentiometer in the gain amplifier circuit 43c the device can be calibrated in vitro, with standard alcohol solutions, to indicate alcohol concentrations in the blood. Referring to FIGS. 3 and 4, the potential-control circuit 14 shown in FIG. 3 interfaces with a custom designed programmable datalogger card 35, as shown in FIG. 4, of similar size and current drain (100 $\mu$A); both are powered, in a preferred embodiment, by a 6-V ½ AA-size battery 36d. A typical data acquisition-recording device 35 that has been successfully used is sold by ONSET Computers, Falmouth, Mass., and sold under the product name of "TATTLETALE LITE®." The sensor assembly 11 with its control circuit 14 is also designed to yield a current or voltage signal proportional to alcohol flux that could be used to continuously transmit the data to a remote receiving device or central monitoring station or unit.

The potential- and diffusion-controlled sensor assembly 11 or transdermal alcohol sensing instrument 10 is applied directly to the skin. Ethanol permeating the skin, and in perspiration, is in approximate equilibrium with BAC. The sensor housing 20 defines a small gas volume between the skin and the diffusion-control membrane 16; alcohol vapor proportional to BAC permeates the diffusion-control membrane 16 to the sensing electrode 12a and is rapidly electrochemically oxidized.

The transdermal alcohol sensor assembly 11 needs to form an air-tight contact between skin and sensing area of the sensor assembly 11. This seal has to function, depending on the application of the alcohol sensing instrument 10, during time periods from hours up to a week. The sensor or sensor device is designed for intimate contact with the skin and is safe and wearable. Sealing to the skin as well as use of skin-compatible materials (polyethylene, TEFLON®) and smooth surfaces (rounded, tapered) are unique design features of the device. Medical adhesive rings (Avery #2230) have been successfully used to seal the sensor to the skin. Elastic belts, tapes or bands can be used to hold the sensor assembly 11 or sensor instrument 10 in intimate contact with the skin.

A miniaturized version of the transdermal alcohol sensing instrument 10 may be worn on the wrist or ankle. This alternative embodiment is illustrated in FIG. 5. The electronics for potential control 14 and data acquisition/storage circuit 35 are miniaturized as a hybrid circuit 39. The sensor 11, the batteries 40 and the hybrid circuit 39 are distributed on a wristband 46. The schematic shows the hybrid circuit 39, with a sensor assembly 11 and a communication port 52 for remote or integral sensing and recording. The sensor assembly 11 is placed on the underside of the wristband 46 which applies contact pressure on an adhesive or rubber ring to assist sealing of the sensor assembly 11 to the skin. The hybrid measurement and datastorage electronics 39 is distributed around the wrist with coin-type batteries 40 for power supply, to maximize comfort and wearability. This embodiment may incorporate an optional data display 48.

The contour of the miniaturized transdermal alcohol sensing instrument can be given a smoother exterior by enclosing the components in an encasing material 45. This embodiment is shown in FIGS. 6(a) and 6(b). The encasing material may be a hard plastic or metal, or a softer elastomeric polymer.

The air-tight seal between skin and sensing area can also be enhanced if the encasing material 45 surrounding the sensing area is a softer composition. In the embodiment shown in FIGS. 5 and 6(a) the hybrid circuit 39 is positioned in use on one side of the wrist, arm or leg and the sensor assembly 11 is positioned on the opposite side of the wrist, arm or leg so that the overall profile of the device is thinner. Batteries 40 are also provided to power the hybrid circuit 39. When the sensor assembly 11, and the hybrid circuit 39 are placed on top of each other, as shown in FIG. 6(b) there is intimate electrical contact, and thus the signal distortions resulting from surrounding electromagnetic fields, are minimized. The configuration shown in FIG. 6(b) would be a preferred configuration for the best signal-to-noise ratio since signal distortion is expected to decrease with decreasing distance between sensor and signal collecting electronics.

The encasing material 45 can be configured as a cover or lid 70 and a base 71 as shown in FIGS. 6(a) and 6(b). The lid 70 can be placed over the hybrid circuit 39 by connecting the lid 70 at hinge 72 to base 71 and securing the lid 70 at snap closure 74. This lid 70 allows batteries and sensors to be easily replaced and enables data to be downloaded through communication port 52.

The sensor sealing interface 44 in any of the embodiments illustrated can be homogeneous, i.e., adhesive or rubber, or can consist of a thin layer of a flexible material, i.e., a polymer or metal foil, forming a container, which can be filled with air, water, or gel, which will cause the material to conform with the skin surface when pressure is applied, and will form an air-tight seal around the sensing area.

The sensor assembly 11 surface in contact with the skin must be large enough to distribute the applied pressure onto the skin, thus avoiding the development of skin irritation. The edges of the material facing the skin should be rounded, or chamfered, or beveled in order to avoid pressure points on the skin surface, which could result in skin pressure sores.

For short-term measurements, the sensing instrument 10 could be held by hand to the skin on any part of the body, i.e., to estimate BAC values by measuring transdermal alcohol in the palm of the hand. For long-term measurements, the sensing instrument 10 could be mounted to the skin by elastic bands, or belts, to arm, leg, body, head. The sensor assembly 11 could also be incorporated in clothing, such as gloves, hats, shirts, glasses, etc. The sensor instrument 10 can also include a display 48, and/or an audible alarm. The display is shown in FIG. 5. The alarm would be a part of the electronics which would be activated when a set alcohol level is reached or exceeded.

As shown in FIGS. 5 and 6, the skin conductivity 17 and/or skin temperature sensors 21a can be placed on and/or close to the surface of the sensor housing 20 facing the skin (FIGS. 1 and 2), inside and/or outside the sensing area, and/or on the air-tight seal-forming surface of the material 44 which surrounds the sensing area.

Measured alcohol values can be displayed directly on the display 48, and/or on-line transmitted to a central signal processing unit, and/or, stored and subsequently transferred to data processors, and/or compared electronically to a pre-set threshold value, resulting in an optical, audible, or electrical alarm.

This unique electrochemical transdermal alcohol sensor, with modifications to the 1) sensing electrode material, 2) permselective membrane, and 3) potential or potentials applied to the sensing electrode could also be used by those skilled in the art to detect low concentrations of other gases, vapors, or other species permeating through the skin such as $O_2$, $CO_2$, acetone, glucose, salts, esters, aldehydes, CO, and oxides of nitrogen. Also, certain blood species such as glucose could be converted with a selective biological or chemical species to ethanol which could be sensed through the skin, thus the electrochemical transdermal alcohol sensor of this invention could be used as a non invasive indicator of blood glucose levels.

The following non-limiting examples will further define the invention described above:

EXAMPLE 1
In Vitro Measurement of Ethanol with the Solid Polymer Electrolyte Transdermal Alcohol Sensor (TAS)

Figure 7:
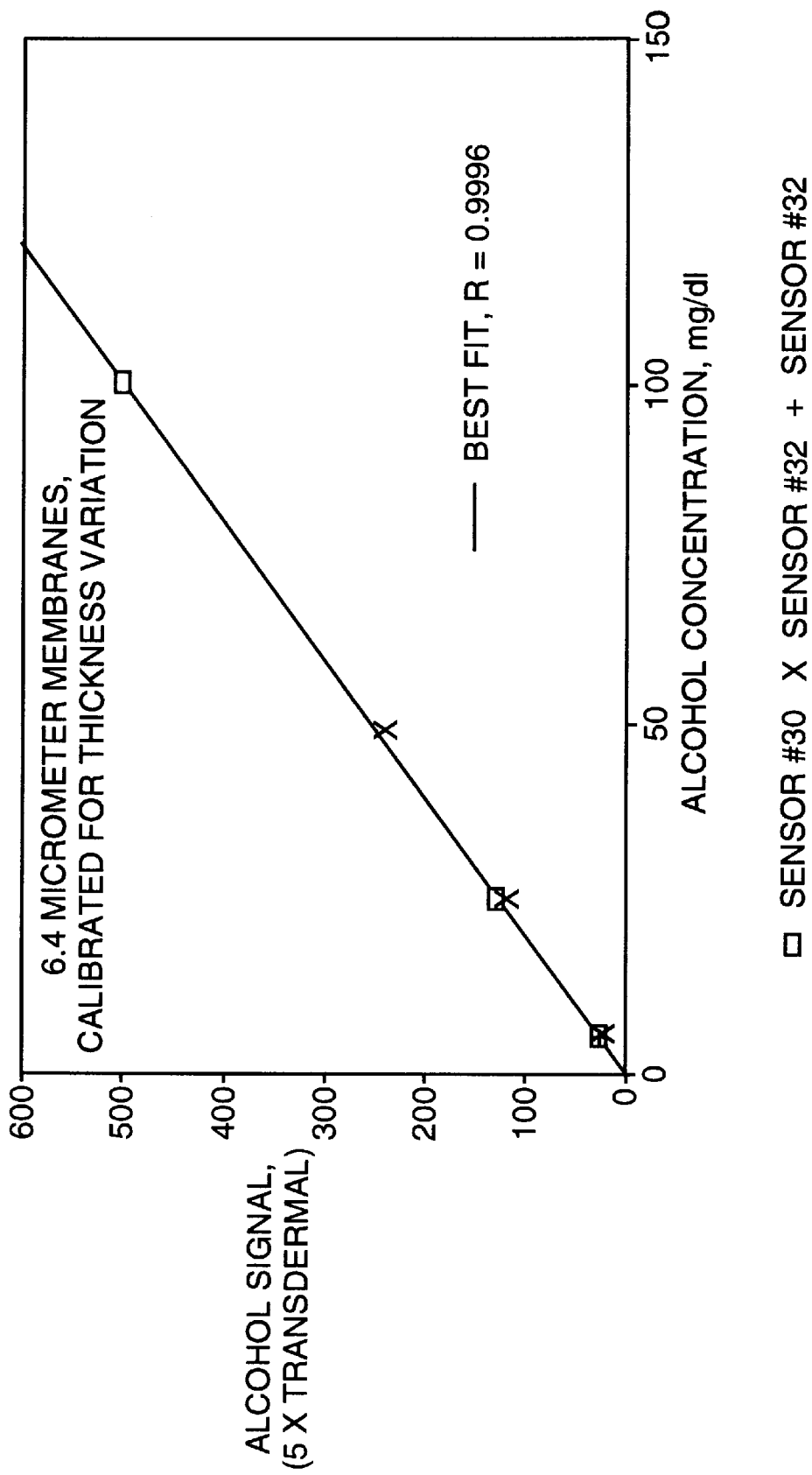
FIG. 7 is a graph of the response of the alcohol sensor shown in FIG. 1 with the diffusion-controlled membrane at steady state.
Figure 9:
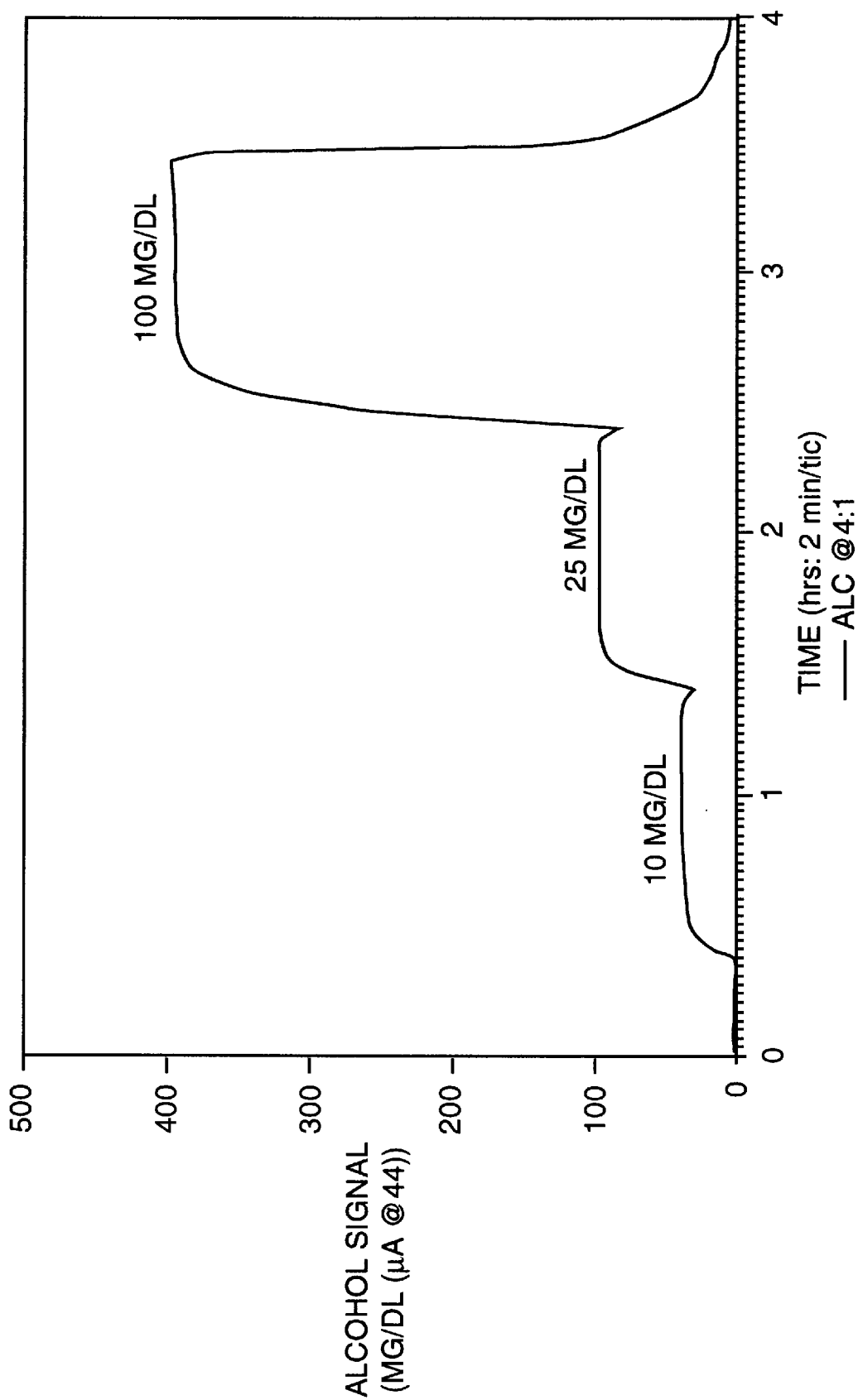
FIG. 9 is a graph of the calibration at a 4-1 ratio for the in vitro alcohol sensor shown in FIG. 1.

FIG. 7 shows the signal of 3 sensors 10 exposed to solutions of different concentrations of ethanol in water. The sensors are held in a temperature-controlled plastic holder and allowed to equilibrate. The graph of the steady current against ethanol concentration is linear over the tested concentration range of ethanol (R=0.99). Experiments with higher ethanol concentrations show linearity of signal response to >1000 mg/dl. The sensor 10 is calibrated by potentiometer adjustment to compensate for the particular diffusion-limiting barrier membrane used in the sensor 10, and for the anticipated in-vitro-to-transdermal ratio (e.g., 100 mg/dl="500"). The response time to rapid changes in ethanol concentration is typically on the order of several minutes and is dependent upon the thickness of the diffusion-control membrane. A typical response-time curve for a sensor 10 is shown in FIGS. 8 and 9.

EXAMPLE 2
Transdermal Measurement of Alcohol Consumption in Humans with the Solid Polymer Electrolyte Transdermal Alcohol Sensor (TAS)

Clinical testing of the TAS has demonstrated that they can track alcohol consumption patterns over long time periods and can detect small BAC levels, down to 10 mg/dl, and even lower with modified sensors, as discussed below.

Figure 10:
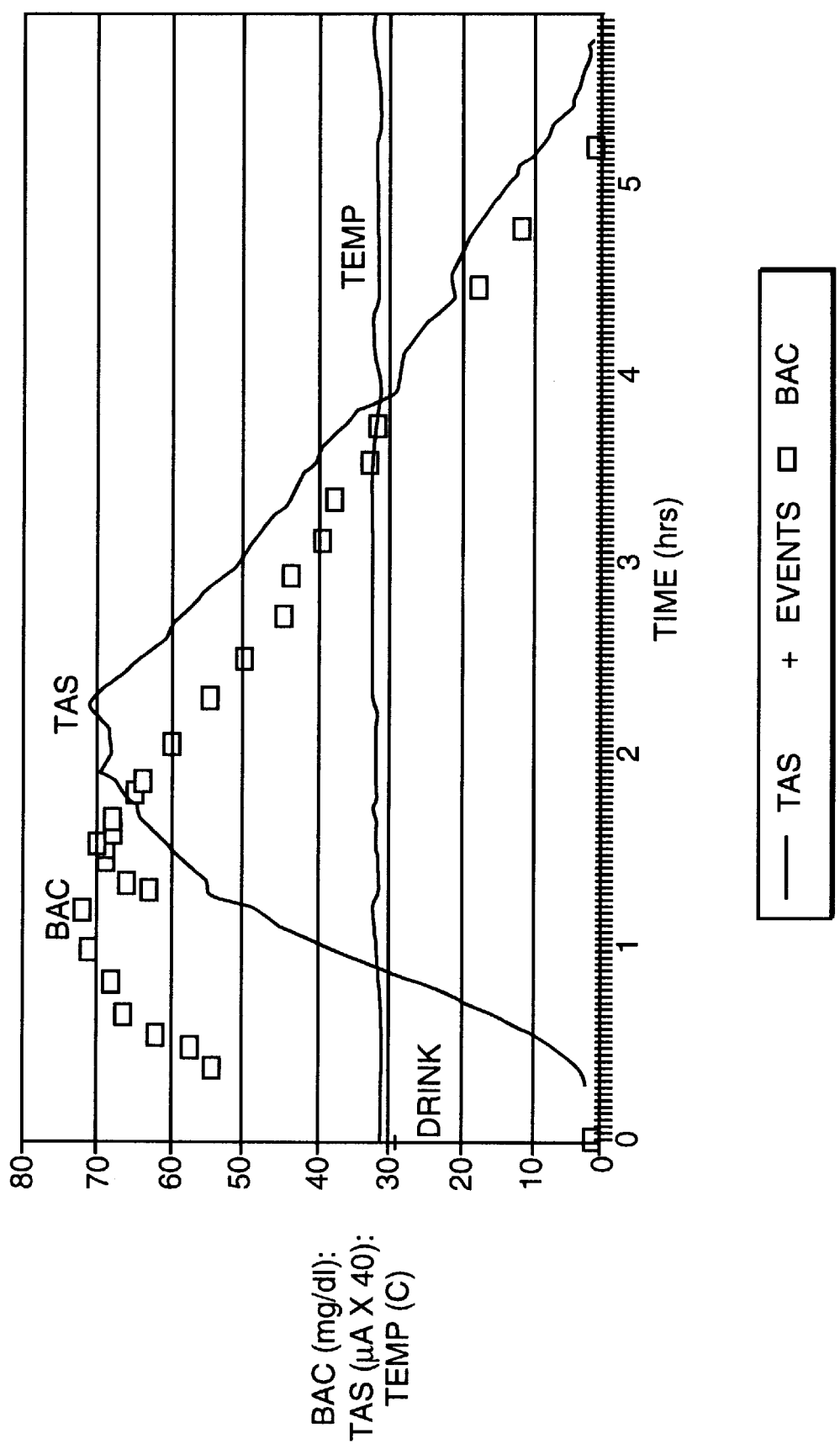
FIGS. 10 and 11. are graphs of an alcohol record taken using the transdermal alcohol sensor shown in FIG. 1.
Figure 11:
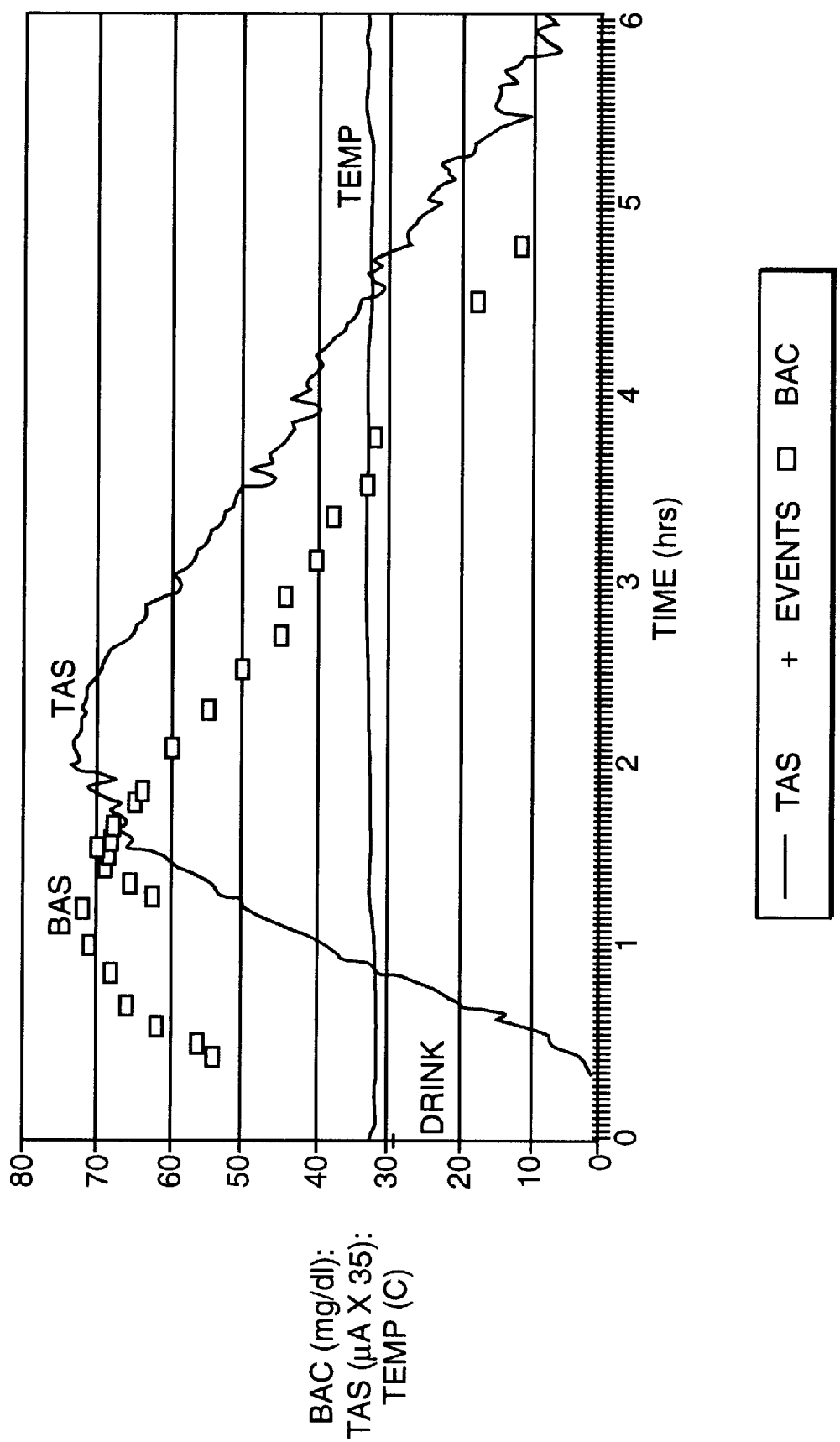

The TAS performance was assessed on volunteers during controlled alcohol consumption in the clinical setting. The device was applied and sealed to the skin with an adhesive ring and held in place with an elastic belt. The subjects consumed from 0.1 to 0.75 ml/kg absolute ethanol delivered as 95% ethanol in 2 to 4 parts juice over a 10- to 20-minute period. Breath alcohol concentrations were measured frequently (e.g., 10-minute intervals) with an Intoximeter 3000 (Intoximeter, Inc.) for comparison. The following figures show the sensor 10 signal in mg/dl (the continuous trace), the BAC measurement in mg/dl (open square symbols), and the temperature in °C. (horizontal line as marked), all on the Y-axis. The event marks (+) denote beginning of alcohol consumption. FIGS. 10 and 11 display the outputs of two similar devices (TAS#34 and TAS#37), simultaneously used to monitor alcohol consumption (0.75 ml/kg) in the same subject, but at different anatomic locations, yielding highly similar sensor 10 curves, in amplitude and time course. In all cases, the sensor 10 signal shows a similar pattern and relative amplitude as the blood (breath) alcohol curve. The TAS ethanol-concentration vs. time curve lags 30 to 45 minutes behind the BAC determined by an Intoximeter. Delays between BAC and TAS measurements, with a modified sensor, have been shortened to less than 10 minutes, as shown in FIG. 12.

Figure 12:
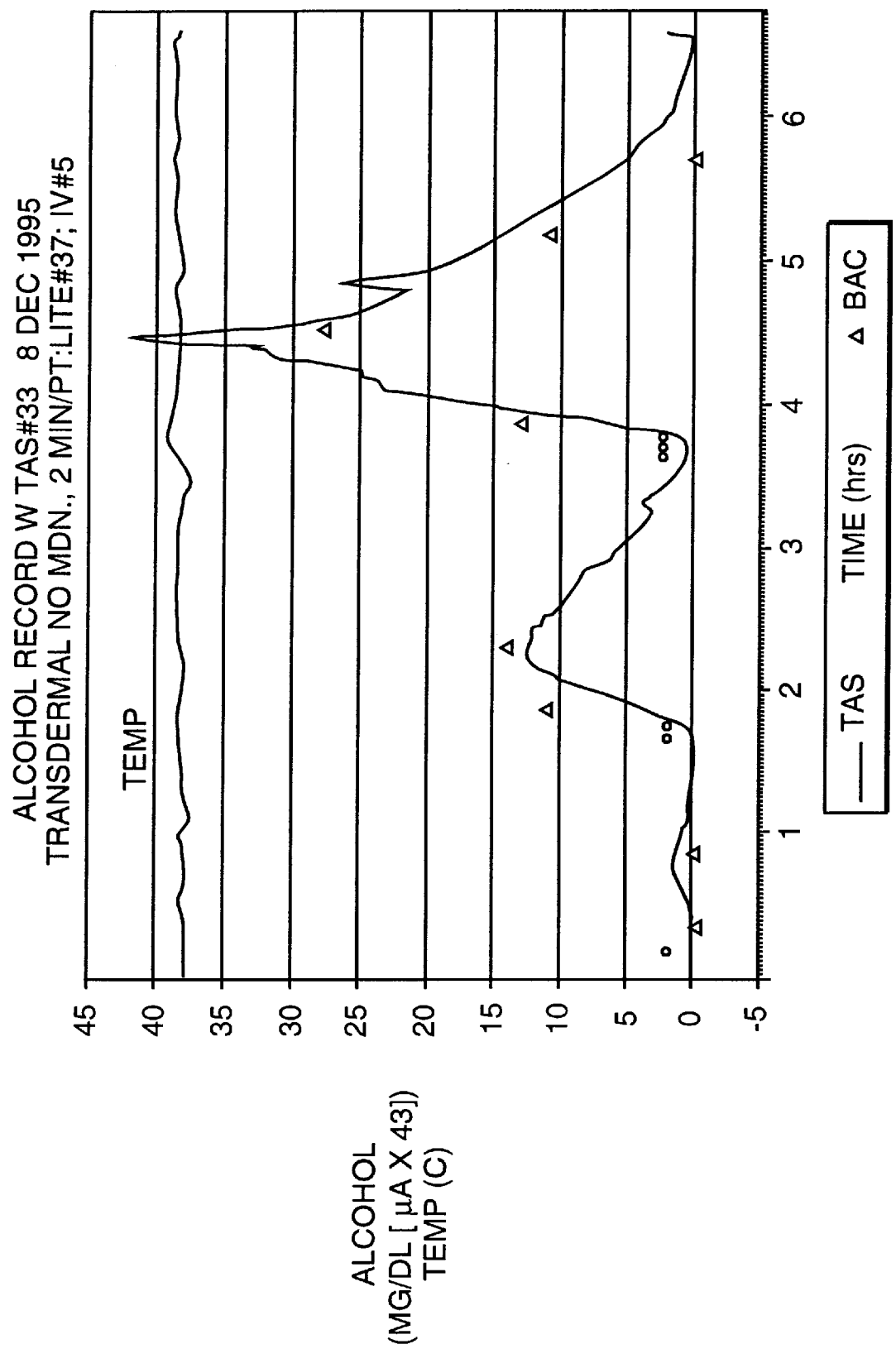
FIG. 12 is a graph of a record generated by the transdermal alcohol sensor shown in FIG. 1 of alcohol administered intravenously.

FIG. 12 shows that the TAS is superior to breath and blood alcohol measurement methods for assessing concentrations of alcohol below 10 mg/dl, where BAC measurements become unreliable. A fast-responding TAS sensor design was used for this study, which shows delays between the BAC and the TAS measurements which are well below the 10-minute range.

Figure 13:
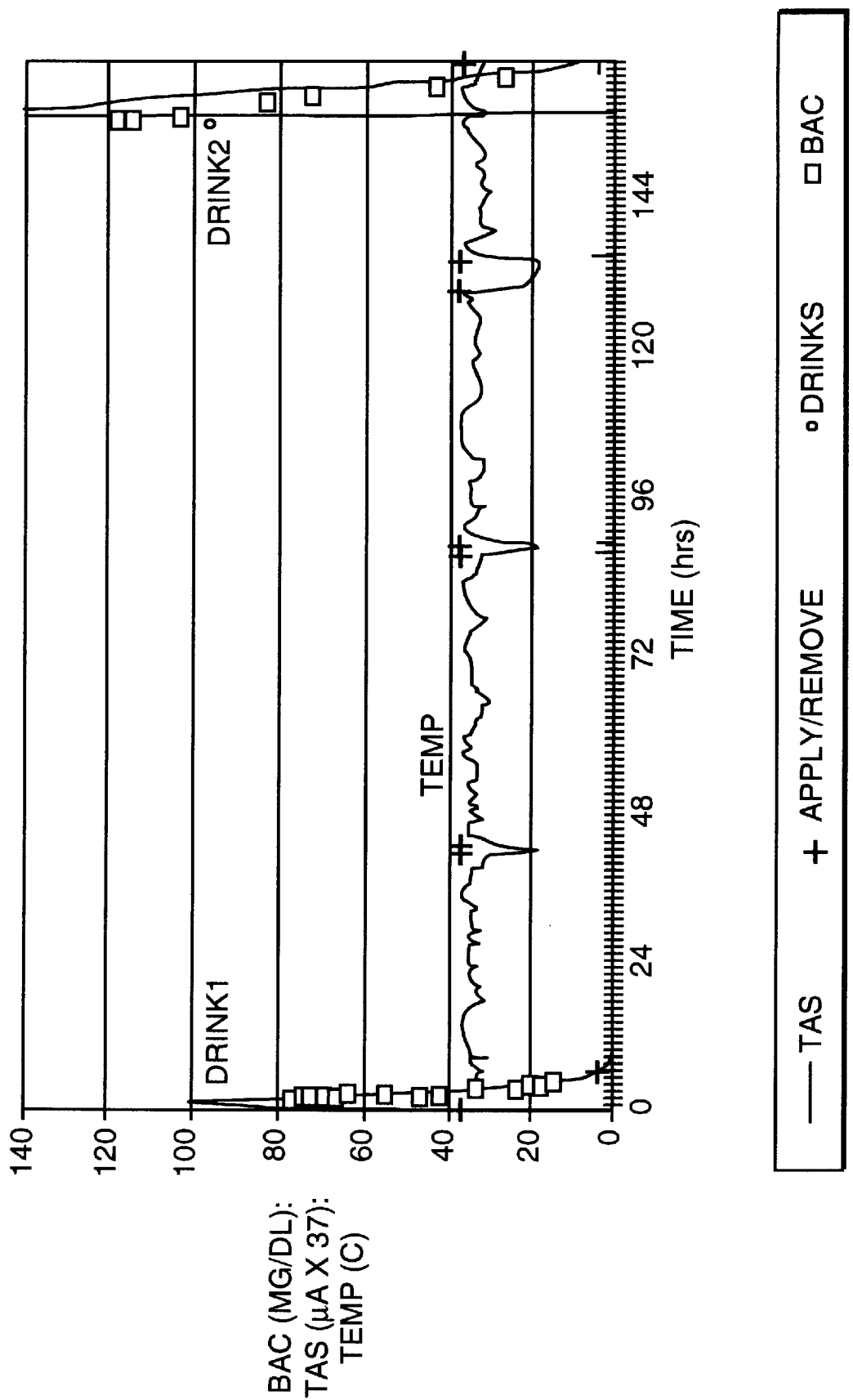
FIG. 13 is a graph of an alcohol record for a seven day study generated with the transdermal alcohol sensor shown in FIG. 1.

To explore ethanol consumption over a longer period outside of the laboratory, non-alcoholic subjects wore the devices for 5 to 7 days. Subjects consumed, or remained abstinent from, alcohol according to their usual custom and identified consumption by pressing an event marker on the TAS. FIG. 13 shows the TAS curve from a 7-day study. The subject consumed 0.75 ml/kg ethanol in the laboratory on Day 1 and then consumed an identical dose of ethanol at home on Day 6. BACs were determined with the Intoximeter in the laboratory and with a portable breathalyzer in the home setting. The TAS was worn continuously on the lower extremity except for periods of planned removal and reapplication (shown by +marks). The peaks of the TAS curves are greater than the peaks of the corresponding BAC curves, but the data are within the range of uncertainty of those devices. No degradation in the TAS signal was observed, suggesting that the TAS can give reliable results under conditions of extended wearing. Transient noise is clearly resolvable from movements and drinking events. The temperature curve tracks well the TAS application and removal events.

Wearing of the TAS was well tolerated by all subjects. No skin irritation or rashes developed on skin over the area of the sensor cell.

Figure 14:
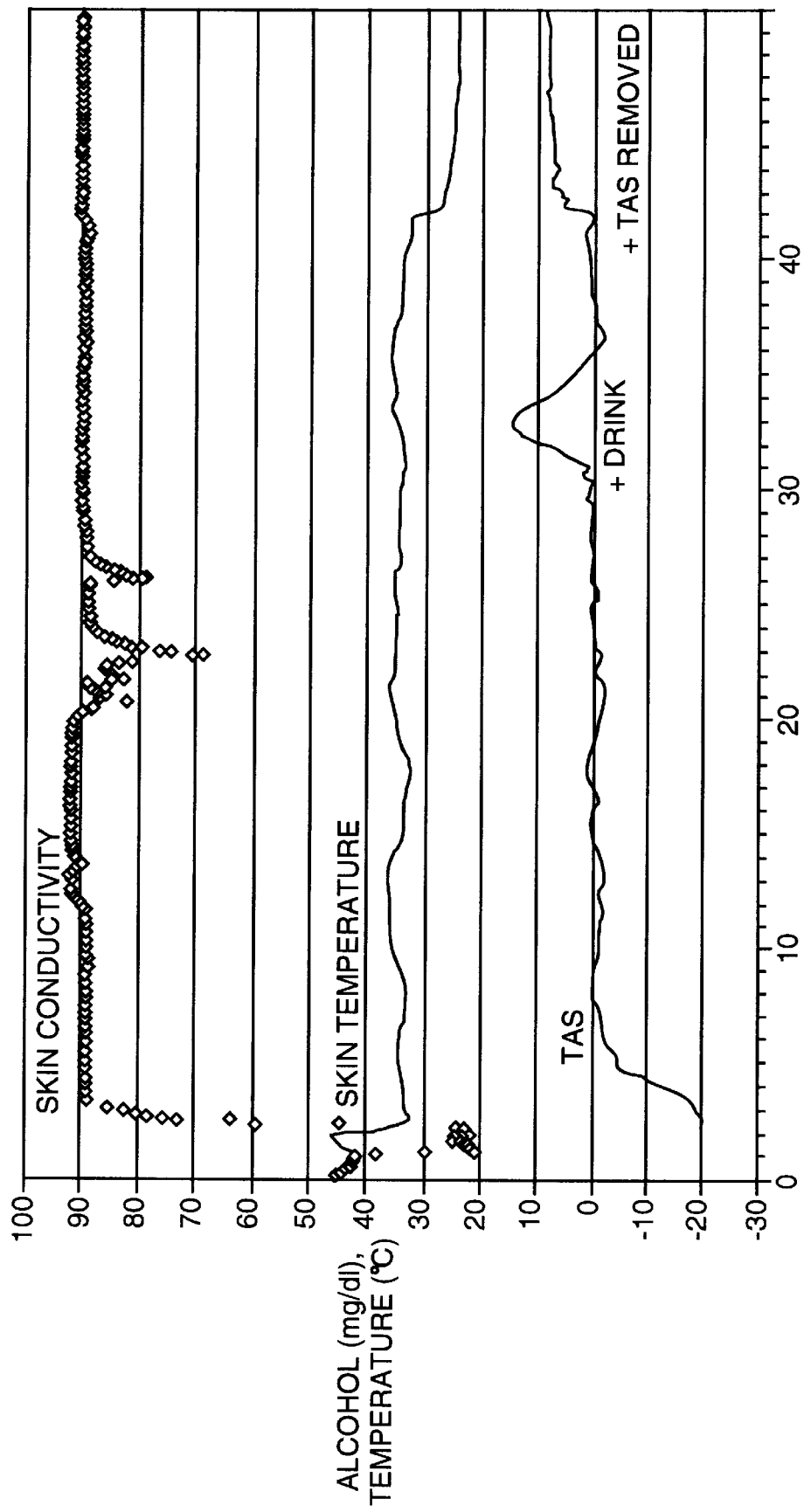
FIG. 14 is a graph generated by the transdermal alcohol sensor shown in FIG. 1 showing simultaneous 48-hour measurement of alcohol, temperature and skin conductivity.

In FIGS. 10–13, the TAS were assembled and tested with imbedded thermistor 21a and 21b in the sensor cell housing and used to determine the TAS are in continuous contact with the skin and to compensate for temperature changes. The results clearly show that temperature response signal is a good indicator of when the TAS is worn or removed. A TAS was fabricated similar to those used to generate the data for FIGS. 10 to 13, except it also contained galvanic microelectrodes 17 at the sensor cell/skin interface to indicate conductivity and continuous contact with the skin. The test results are depicted in FIG. 14 and show a signal indicating conductivity and continuous contact with the skin.

While the foregoing invention has been described with reference to its preferred embodiments, various alterations and modifications will occur to those skilled in the art. For example, where very low alcohol levels must be detected quickly (10 minutes or less) and semiquantative measures are acceptable, the human stratum corneum membrane alone can act as a diffusion-limiting membrane as in FIG. 12 and there will be a small gas volume between the sensing electrode and the human stratum corneum membrane. In such embodiment, the sensor cell 11 can be protected from perspiration by covering it with a porous membrane such as that sold by Norton Performance Plastics, Norton, N.J. (Zitex, 1064-122D), instead of the solid plastic film diffusion-control membrane 16. In addition, it would be obvious to those skilled in the art that other electrolytes such as acid or bases in a solid polymer, gelled or liquid electrolyte form could also be used. Also, alternative processes for maintaining the sensing electrode near the Pt/air ($O_2$) rest potential, 1.06 V, can be based on two-electrode systems such as 1) applying a predetermined fixed voltage between the sensing electrode and a stable combined counter/reference electrode (e.g. $PtO_2$, $Pt/H_2$) and measuring the current when alcohol is consumed at the sensing electrode or 2) galvanically connecting the sensing electrode through a known resistor to a stable combined counter/reference electrode (e.g. $PtO_2$, Pt/Air ($O_2$) and measuring the current generated by the cell when the alcohol is electrochemically consumed at the sensing electrode. In addition, it would be obvious to those skilled in the art that alternative catalyst and electrodes such as Pt-Ir, Pt, Ru, Pd, Au or C could be used as sensing, counter or reference electrodes. Also, the transdermal alcohol sensor could easily be combined with ultrasound, electrotransport, electroporation or other processes that facilitate alcohol transport through the skin, leading to minimal or no delay between the BAC and the TAS measurements. These and all other such modifications and alterations are intended to fall within the scope of the appended claims.

What is claimed is:

1. A transdermal alcohol sensing instrument comprising:

a sensor cell for measuring ethanol vapor at the surface of the skin of a person being monitored;

a potential control circuit for controlling the operation of said sensor cell;

at least one diffusion-control membrane mounted over the sensor cell on the side of said sensor cell designed to contact the skin of the person being measured, said diffusion-control membrane having a lower ethanol permeability than the human stratum corneum, said diffusion-control membrane controlling ethanol and water vapor flux from the skin to the sensor cell.

2. The transdermal alcohol sensing instrument of claim 1, wherein said sensor cell is based on an electrochemical solid polymer electrolyte membrane in a proton exchange form.

3. The transdermal alcohol sensing instrument of claim 2, wherein said sensor cell comprises a sensing electrode which is maintained at a fixed anodic potential equal to or above the Pt/air rest potential.

4. The transdermal alcohol sensing instrument of claim 3, further comprising a potentiostatic circuit for controlling the sensing electrode.

5. The transdermal alcohol sensing instrument of claim 1, further comprising a sensor cell that electrochemically oxidizes ethanol vapor permeating from the skin of the person being measured and concurrently generates a corresponding electrical output signal that is recorded continuously as it is generated at a fixed time interval of 10 to 30 seconds for a plurality of days.

6. The transdermal alcohol sensing instrument of claim 1, wherein said sensor cell comprises a sensing electrode, a reference electrode and a counter electrode.

7. The transdermal alcohol sensing instrument of claim 1, further comprising a wrist band and a power supply, said sensing instrument and power supply being mounted on said wrist band.

8. The transdermal alcohol sensing instrument of claim 1, further comprising a arm band and a power supply, said sensor and power supply being mounted on said arm band.

9. The transdermal alcohol sensing instrument of claim 1, further comprising at least one thermistor for monitoring temperature.

10. The transdermal alcohol sensing instrument of claim 1, further comprising microelectrodes positioned near a sensor cells/skin interface to measure electrical ionic continuity along the skin surface to indicate whether the sensing instrument has been removed from the skin.

11. The transdermal alcohol sensing instrument of claim 1, further comprising a display for displaying measured alcohol values directly at the instrument.

12. The transdermal alcohol sensing instrument of claim 1, further comprising a data recorder for monitoring and quantifying patterns of alcohol consumption over a period of time.

13. The transdermal alcohol sensing instrument of claim 1 wherein said membrane controls water-vapor flux and evaporation to manage humidification of the solid polymer electrolyte membrane and sensor cell.

* * * * *